United States Patent [19]

Sih

[11] 4,269,995
[45] May 26, 1981

[54] 19,20-DIDEHYDRO-13,14-DIHYDRO-PG$_2$ COMPOUNDS

[75] Inventor: John C. Sih, Kalamazoo, Mich.

[73] Assignee: The Upjohn Company, Kalamazoo, Mich.

[21] Appl. No.: 85,621

[22] Filed: Oct. 17, 1979

Related U.S. Application Data

[62] Division of Ser. No. 26,066, Apr. 2, 1979, Pat. No. 4,243,611.

[51] Int. Cl.$^3$ .......................................... C07C 177/00
[52] U.S. Cl. ................................... 560/121; 502/503; 260/404; 260/404.5; 260/408; 260/410; 260/410.4 R; 260/410.5; 260/413

[58] Field of Search ....................... 560/121; 562/503; 260/404, 404.5, 408, 410, 410.5, 410.9 R, 413

[56] References Cited

FOREIGN PATENT DOCUMENTS 2635985  2/1978  Fed. Rep. of Germany ........... 560/121

*Primary Examiner*—Robert Gerstl
*Attorney, Agent, or Firm*—Robert A. Armitage

[57] ABSTRACT

The present invention provides novel 19,20-didehydro-13,14-dihydro-PG$_2$ compounds, methods for their preparation and pharmacological use for the induction of prostaglandin-like effect.

1 Claim, No Drawings

19,20-DIDEHYDRO-13,14-DIHYDRO-PG$_2$ COMPOUNDS

CROSS REFERENCE TO RELATED APPLICATIONS

The present application is a division of Ser. No. 026,066, filed Apr. 2, 1979, now U.S. Pat. No. 4,243,611.

BACKGROUND OF THE INVENTION

The present invention relates to novel prostaglandin analogs. Particularly, these compounds are analogs of the prostaglandins wherein the C-20-C-19 position is unsaturated, i.e., 19,20-didehydro-PG compounds. Most particularly, the present invention relates to novel 19,20-didehydro-13,14-dihydro-PG$_2$ compounds, a disclosure of the preparation and use of which is incorporated here by reference from U.S. Pat. No. 4,228,104.

Prior Art

Prostaglandin analogs exhibiting unsaturation in the C-17, C-18, or C-20 position are known in the art. See, for example, U.S. Pat. No. 3,919,285 German Offenlegungsschrift No. 2,635,985 (and its corresponding Derwent Farmdoc CPI No. 10302A), and U.S. Pat. No. 4,064,351 for examples of such compounds. See also the references cited in U.S. Ser. No. 026,066.

SUMMARY OF THE INVENTION

The present invention particularly provides:
A compound of the formula

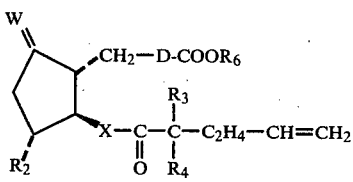

wherein D is
(1) cis—CH=CH—CH$_2$—(CH$_2$)$_g$—CH$_2$—,
(2) cis—CH=CH—CH$_2$—(CH$_2$)$_g$—CF$_2$—,
(3) cis—CH$_2$—CH=CH—CH$_2$—CH$_2$—,
(4) trans—(CH$_2$)$_3$—CH=CH—, wherein g is zero, one, 2, or 3,
wherein Q is

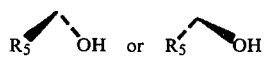

wherein R$_5$ is hydrogen or methyl,
wherein R$_6$ is (a) hydrogen, (b) alkyl of one to 12 carbon atoms, inclusive, (c) cycloalkyl of 3 to 10 carbon atoms, inclusive, (d) aralkyl of 7 to 12 carbon atoms, inclusive, (e) phenyl, (f) phenyl substituted with one, 2, or 3 chloro or alkyl groups of one to 3 carbon atoms, inclusive;

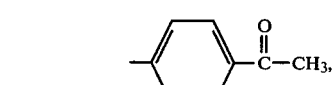

(g)

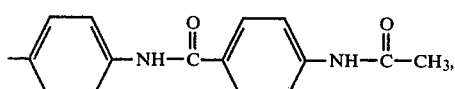

(h)

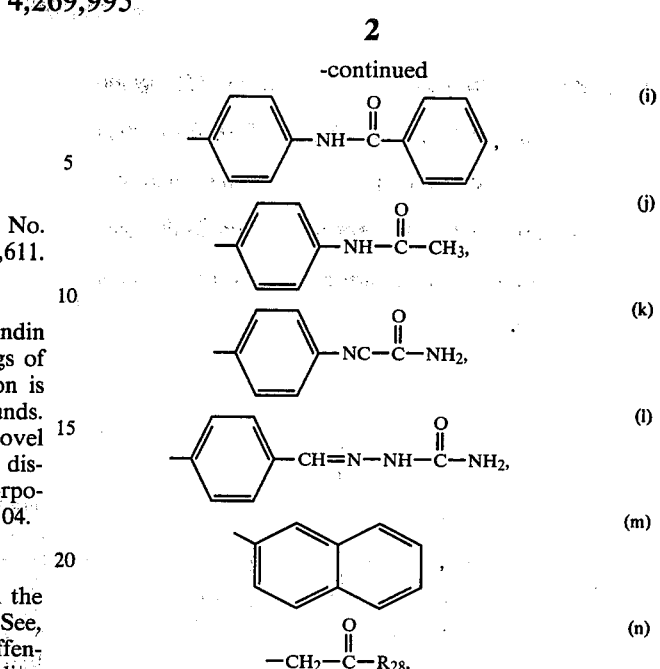

wherein R$_{28}$ is phenyl, p-bromophenyl, p-biphenylyl, p-nitrophenyl, p-benzamidophenyl, or 2-naphthyl, or
(o) a pharmacologically acceptable cation;
wherein R$_2$ is hydrogen, hydroxyl, or hydroxymethyl; r wherein R$_3$ and R$_4$ are hydrogen, methyl, or fluoro, being the same or different, with the proviso that one of R$_3$ and R$_4$ is fluoro only when the other is hydrogen or fluoro;
wherein W is

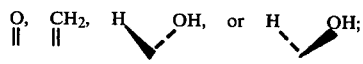

and wherein X is —CH$_2$CH$_2$—.

The compounds of the present invention are particularly useful for inducing prostaglandin-like biological effects, as is described in U.S. Ser. No. 026,066. Uses of compounds in accordance with the present invention include, therefore, anti-asthmatic indication.

I claim:
1. A compound of the formula

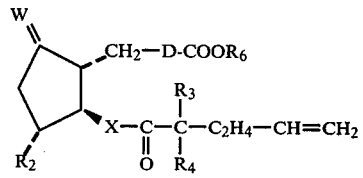

wherein D is
(1) cis—CH=CH—CH$_2$—(CH$_2$)$_g$—CH$_2$—,
(2) cis—CH=CH—CH$_2$—(CH$_2$)$_g$—CF$_2$—,
(3) cis—CH$_2$—CH=CH—CH$_2$—CH$_2$—,
(4) trans—(CH$_2$)$_3$—CH=CH—, wherein g is zero, one, 2, or 3;
wherein Q is

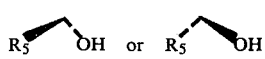

wherein R$_5$ is hydrogen or methyl, wherein $R_6$ is (a) hydrogen, (b) alkyl of one to 12 carbon atoms, inclusive, (c) cycloalkyl of 3 to 10 carbon atoms, inclusive, (d) aralkyl of 7 to 12 carbon atoms, inclusive, (e) phenyl, (f) phenyl substituted with one, 2, or 3 chloro or alkyl groups of one to 3 carbon atoms, inclusive;

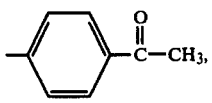  (g)

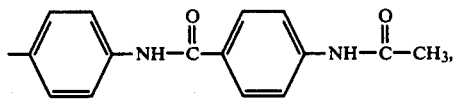  (h)

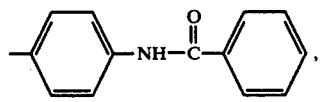  (i)

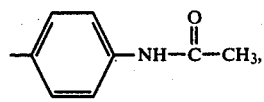  (j)

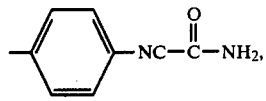  (k)

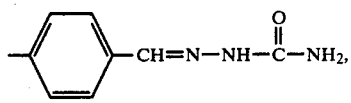  (l)

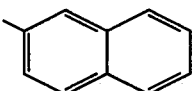  (m)

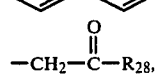  (n)

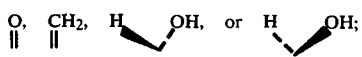

wherein $R_{28}$ is phenyl, p-bromophenyl, p-biphenylyl, p-nitrophenyl, p-benzamidophenyl, or 2-naphthyl, or (o) a pharmacologically acceptable cation;
wherein $R_2$ is hydrogen, hydroxyl, or hydroxymethyl;
wherein $R_3$ and $R_4$ are hydrogen, methyl, or fluoro, being the same or different, with the proviso that one of $R_3$ and $R_4$ is fluoro only when the other is hydrogen or fluoro;
wherein W is $$\overset{O}{\underset{\|}{}}, \quad \overset{CH_2}{\underset{\|}{}}, \quad \overset{H}{\diagup}\hspace{-0.3em}\overset{OH}{\diagdown}, \quad \text{or} \quad \overset{H}{\diagdown}\hspace{-0.3em}\overset{OH}{\diagup};$$

and wherein X is $-CH_2CH_2-$.

* * * * *

UNITED STATES PATENT OFFICE
CERTIFICATE OF CORRECTION

Patent No. 4,269,995     Dated   26 May 1981

Inventor(s)   John C. Sih

It is certified that error appears in the above-identified patent and that said Letters Patent are hereby corrected as shown below:

Column 2, lines 11-14, and Column 4, lines 2-6, should read as follows:

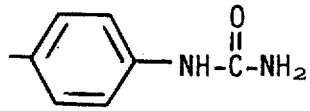

Signed and Sealed this

Twenty-seventh Day of October 1981

[SEAL]

Attest:

Attesting Officer

GERALD J. MOSSINGHOFF

Commissioner of Patents and Trademarks